United States Patent [19]

Steck et al.

[11] Patent Number: 5,250,556
[45] Date of Patent: Oct. 5, 1993

[54] MICROBICIDAL COMPOSITIONS

[75] Inventors: Bernhard Steck, Muntelier; Robert Nyfeler, Basel, both of Switzerland

[73] Assignee: Ciba-Geigy Corporation, Ardsley, N.Y.

[21] Appl. No.: 791,861

[22] Filed: Nov. 13, 1991

[30] Foreign Application Priority Data

Nov. 16, 1990 [CH] Switzerland .................. 3637/90-3

[51] Int. Cl.$^5$ ...................... A01N 43/36; A01N 43/64
[52] U.S. Cl. ...................... 514/383; 514/422
[58] Field of Search .................... 514/383, 422

[56] References Cited

U.S. PATENT DOCUMENTS

| | | | |
|---|---|---|---|
| 4,705,800 | 11/1987 | Nyfeler et al. | 514/422 |
| 4,723,984 | 2/1988 | Holmwood et al. | 71/76 |
| 4,845,112 | 7/1989 | Brandes et al. | 514/383 |
| 5,063,241 | 11/1991 | Brandes et al. | 514/383 |

FOREIGN PATENT DOCUMENTS 0052424  5/1982  European Pat. Off. .

OTHER PUBLICATIONS

Nyfeler et al, C.A. vol. 107 (1987) 107:2683b.

Primary Examiner—Allen J. Robinson
Attorney, Agent, or Firm—Edward McC. Roberts; Marla J. Mathias

[57] ABSTRACT

The combination of the plant microbicide 4-(2,2-difluoro-1,3-benzodioxol-7-yl)-1H-pyrrole-3-carbonitril with the plant microbicide α-[2-(4-chlorophenyl)ethyl]-α-(1,1-dimethyl-ethyl)-β-(1H-1,2,4-triazolyl)-1-ethanol results in a synergistically enhanced effect in the control of plant diseases. Microbicidal compositions based on such combinations are suitable for treating natural products of vegetable and animal origin and, in particular, for seed treatment.

11 Claims, No Drawings

MICROBICIDAL COMPOSITIONS

The present invention relates to microbicidal mixtures with a synergistically enhanced action against plant diseases and against attack by microorganisms of plant propagation material or other vegetable or animal material, and to processes for applying such mixtures, in particular for seed dressing.

In particular, the invention relates to the control, or prevention, of diseases on cereal seeds.

It has been found that a combination of component I), 4-(2,2-difluoro-1,3-benzodioxol-7-yl)-1H-pyrrol-3-carbonitrile, of formula I

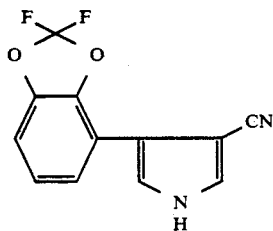

with component II), α-[2-(4-chlorophenyl)ethyl]-α-(1,1-dimethyl-ethyl)-β-(1H-1,2,4-triazolyl)-1-ethanol of formula II

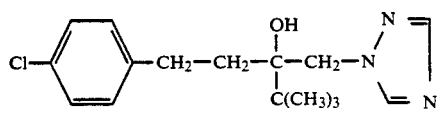

or with a salt thereof, results in synergistically enhanced activity in the control and prevention of plant diseases.

EP-A-206 999 discloses the compound of formula I as a fungicidally active compound. It is distinguished mainly as a contact fungicide.

The compound of formula II is disclosed in EP-A-40 345 as a fungicidally active compound.

The above-mentioned salts of the compound of formula II can be prepared by reacting the base with acids.

The acids which can be used for preparing salts of the formula II include: hydrohalic acid such as hydrofluoric acid, hydrochloric acid, hydrobromic acid or hydroiodic acid, and also sulfuric acid, phosphoric acid, nitric acid, and organic acids such as acetic acid, trufluoroacetic acid, trichloroacetic acid, propionic acid, glycolic acid, thiocyanic acid, lactic acid, succinic acid, citric acid, benzoic acid, cinnamic acid, oxlic acid, formic acid, benzenesulfonic, p-toluenesulfonic acid, methanesulfonic acid, salicylic acid, p-aminosalicylic acid, 2-phenoxybenzoic acid, 2-acetoxybenzoic acid or 1,2-naphthalenedisulfonic acid.

The term salts also comprises metal complexes of the basic component II. These complexes are composed of the basic organic molecule and an inorganic or organic metal salt, for example the halides, nitrates, sulfates, phosphates, acetates, trifluoroacetates, trichloroacetates, propionates, tartrates, sulfates, salicylates, benzoates and the like, of the elements of the second main group of the Periodic Table, such as calcium and magnesium and of the third and fourth main group such as aluminium, tin or lead, and also of the first to eighth auxiliary group, such as chromium, managanese, iron, cobalt, nickel, copper, zinc and the like. The elements of the auxiliary groups of the 4th period are preferred. The metals may exist in different valence states. The metal complexes can be mononuclear or polynuclear, i.e. they can contain one or more parts of the organic molecule as ligands.

It is known to the skilled person that the total action of a fungicide can be broadened by adding another fungicide having a different activity spectrum.

Surprisingly, it has been found that a combination of compounds I and II results in a quite unexpectedly enhanced action against seed-borne and soil-borne fungi. The enhanced action, which is achieved by the combination of the invention, is significantly greater than the activity to be expected by adding the two individual components, that is to say, the activity is synergistically enhanced.

The present invention makes it possible, for example, for seed dressing to be carried out with substantially smaller amounts of biocides than in normal practice and therefore constitutes a material enrichment of the art.

The invention not only relates to the use of mixtures of components I and II for treating seeds, but also to the application of the individual components in immediate succession. Advantageous mixing ratios of the two active substances are I:II=10:1 to 1:20, preferably I:II=10:1 to 1:12 and, most preferably, I:II=4:1 to 1:2. Other advantageous mixing ratios are I:II=5:2 to 2:5 or 5:3, 3:2, 1:1.

The inventive combination of compounds I and II effects a useful contact action as well as a systemic and long-term action of the control of seed- and soil-borne plant diseases. The combinations of the invention destroy the microorganisms on the stored goods and on propagation material, in particular on seeds, and developing plants are protected against attack by the soil-borne microorganisms.

The mixture of the invention are effective against the phytopathogenic fungi which belong to the following classes: Ascomycetes [for example the genera Erysiphe, Sclerotinia, Monilinia, Helminthosporium (=Drechslera), Mycosphaerella, Pyrenophora]; Basidiomycetes (for example the genera Ustilago, Puccinia, Tilletia, Rhizoctonia); Fungi imperfecti (for example the genera Fusarium, Botrytis, Pyricularia, Septoria, Phoma, Alternaria). The combinations of the invention are particularly effective in seed treatment (fruit, tubers, grains), and the action against *Fusarium nivale* on wheat is particularly pronounced. However, they are also suitable for direct treatment of the soil or of the plant or individual parts of the plant. They were well tolerated by plants and are ecologically acceptable.

The mixture of the invention is normally used together with the adjuvants customarily employed in the art of formulation. The compounds of formulae I and II are formulated in known manner to, for example, emulsifiable concentrates, spreadable pastes, directly sprayable or dilutable solutions, dilute emulsions, wettable powders, soluble powders, dusts, granules, and also for encapsulation in, for example polymeric substances. The application methods such as spraying, misting, atomising, broadcasting, brushing or pouring, and the nature of the composition are adapted to suit the intended aims and prevailing circumstances. In general, useful application rates are 0.0005 to not more than 0.5 kg in each case, preferably 0.001–0.01 kg of compounds I and II per 100 kg of goods to be protected. However, the application conditions depend very substantially on the nature (surface area, consistency, moisture content)

of the goods and of the environmental factors to which they are exposed.

Within the scope of this invention, the storage goods which can be protected with the mixture of the invention and, in particular, plant propagation material, specifically seeds, will be understood as meaning natural substances of vegetable and/or animal origin and the processing products thereof for which long-term protection is desired, for example the plants and the parts of these plants which are mentioned below and which have been harvested from the natural life cycle (stalks, leaves, tubers, seeds, fruits, grains) and which are in the freshly harvested state or in processable form (pre-dried, moistened, compressed, comminuted, ground, roasted, etc). Also falling within the scope of the invention is the protection of timber whether it is in the form of raw timber or in the form of finished products (building timber, furniture, electricity pylons, barriers and the like). Storage goods which also fall within the scope of the invention include natural products of animal origin for example hides, skins, hairs and the like.

Target crops in the context of this invention are, for example, the following plant species: cereals: (wheat, barley, rye, oats, rice, sorghum, maize and related crops); beet (sugar and fodder beet); pulses: (beans, lentils, soybeans, peas, coffee); oil crops: (oilseed rape, mustard, poppy, sunflowers); cucurbits: (cucumbers, pumpkin, melons); fibre plants: (cotton, flax); vegetable varieties: (lettuce, cabbage varieties, spinach, carrots, onions, tomatoes, potatoes, red peppers); ornamentals: (tulips, daffodils, dahlias, chrysanthemums and other flowers) and culinary herbs and their seeds.

A preferred process for applying the mixture according to the invention comprises spraying or wetting the detached plant material with a liquid formulation or mixing the plant material with a solid formulation of the active ingredients. These preservation processes fall within the scope of the present invention, as do the wood, the storage goods or plant propagation material which have been treated with said mixture of I and II. The term "plant propagation material" encompasses generative plant material such as seeds and vegetative plant material such as cuttings and tubers (for example potatoes).

The compounds of formulae I and II are used in the practice of this invention in the form of formulations and can be used, if appropriate, together with other carriers which are customary in formulation technology, surfactants or other substances which promote the application of the active ingredients.

Suitable carriers and adjuvants can be solid or liquid and correspond to the substances which are expedient in the art of formulation, for example natural or regenerated mineral substances, solvents, dispersants, wetting agents, tackifiers, thickeners, binders or fertilisers.

In a particularly preferred process, the seed kernels, tubers, fruits or other plant material to be protected (also, for example, wood) are coated with the mixture of the compounds of the formulae I and II either by impregnating the material with a liquid formulation of the active ingredients or by applying a layer of a liquid or a solid to the material. In addition, other types of application are possible in special cases, for example the targeted treatment of cuttings or of twigs which are intended for propagation.

The compound of the formulae I and II are used in unmodified form or, preferably, together with the adjuvants customary in the art of formulation, and they are therefore processed in known manner to emulsifiable concentrates and spreadable pastes (for example for the protection of wood), directly sprayable or dilutable solutions, dilute emulsions, wettable powders, soluble powders, dusts, granules, and also encapsulations, for example in polymeric substances. The application methods such as spraying, misting, atomising, broadcasting, brushing or pouring as well as the nature of the compositions are chosen to suit the intended aims and the prevailing conditions. In general, advantageous application rates in the case of field treatment are 5 g to 5 kg of active ingredient (a.i.) of the formulae I and II per ha; preferably 10 g to 2 kg of a.i./ha, particularly preferably 20 g to 600 g of a.i./ha.

The formulations, i.e. the compositions, preparations or combinations which contain the compounds of formulae I and II and, if appropriate, a solid or liquid additive, are prepared in known manner, for example by intimately mixing and/or grinding the active ingredients with extenders, for example solvents, solid carriers and, if appropriate, surface-active compounds (surfactants).

Suitable solvents are: aromatic hydrocarbons, preferably the fractions $C_8$ to $C_{12}$, for example xylene mixtures or substituted naphthalenes, phthalic esters such as dibutyl phthalate or dioctyl phthalate, aliphatic hydrocarbons such as cyclohexane or paraffins, alcohols and glycols as well as their ethers and esters such as ethylene glycol monomethyl ether, ketones such as cyclohexanone, strongly polar solvents such as N-methyl-2-pyrrolidone, dimethyl sulfoxide or dimethylformamide, and epoxidised and unepoxidised vegetable oils or soybean oil; or water.

The solid carriers used, for example, for dust and dispersible powders are calcite, talc, kaolin, montmorillonite or attapulgite, highly-disperse silica or absorbent polymers. Suitable granulated, adsorptive granule carriers are pumice, crushed brick, sepiolite or bentonite, and examples of suitable nonsorbent carriers are calcite or dolomite.

Depending on the nature of the compounds of formulae I and II to be formulated, suitable surface-active compounds are nonionic, cationic and/or anionic surfactants which have good emulsifying, dispersing and wetting properties. Surfactants will also be understood as meaning mixtures of surfactants.

The surfactants customarily employed in the art of formulation are described, inter alia, in the following publications:

"Mc Cutcheon's Detergents and Emulsifiers Annual" MC Publishing Corp., Glen Rock, N.J., 1988.

M. and J. Ash, "Encyclopedia of Surfactants", Vol. I-III, Chemical Publishing Co., New York, 1980-1981.

Other particularly useful additives which are advantageous for application are natural or synthetic phospholipids of the series of the cephalins and lecithins, for example phosphatidylethanolamine, phosphatidylserine, phosphatidylglycerine, lysolecithin.

The agrochemical formulations contain 0.1 to 99%, particular 0.1 to 95% of compound of the formula I, 99.9 to 1%, in particular 99.9 to 5%, of a solid or liquid adjuvant, and 0 to 25%, in particular 0.1 to 25% of a surfactant.

Whereas commercial products are preferably formulated as concentrates, the end user will normally use dilute formulations.

The present invention also relates to such (agro)-chemical formulations.

The following examples will serve to illustrate the invention, the term "active ingredient" meaning a mixture of compound I and compound II in a specific ratio of 10:1 to 1:11 in the mixture.

| Wettable powder | a) | b) | c) |
|---|---|---|---|
| active ingredient [I:II = 3:2(a), 1:1(b), 1:11(c)] | 25% | 50% | 75% |
| sodium ligninsulfonate | 5% | 5% | — |
| sodium laurylsulfate | 3% | — | 5% |
| sodium diisobutylnaphthalinsulfonate | — | 6% | 10% |
| octylphenol polyethylen glycol ether (7-8 mol ethylene oxide) | — | 2% | — |
| highly-disperse silica | 5% | 10% | 10% |
| kaolin | 62% | 27% | — |

The active ingredient is intimately mixed with the additives and the mixtures is ground thoroughly in a suitable mill, affording wettable powders which can be diluted with water to give suspensions of any desired dilution. Such slurries can be used for wet-dressing reproducible material, for example grain seeds or plant tubers.

| Emulsifiable concentrate | |
|---|---|
| active ingredient (I:II = 2:5) | 10% |
| octylphenol polyethylene glycol ether (4-5 mol ethylene oxide) | 3% |
| calcium dodecylbenzolsulfonate | 3% |
| castor oil polyglycol ether (35 mol of ethylene oxid) | 4% |
| cyclohexanone | 30% |
| xylene mixture | 50% |

Emulsions of any desired concentration which can be used in crop protection but also for protecting wood can be prepared from this concentrate by dilution with water.

| Dusts | a) | b) | c) |
|---|---|---|---|
| active ingredient [I:II = 4:1 (a); 7:1 (b) and 1:1 (c)] | 5% | 8% | 4% |
| talc | 95% | — | — |
| kaolin | — | 92% | — |
| powdered stone | — | — | 96% |

Ready-for-use dusts are obtained by mixing the active ingredient with the carrier and grinding the mixture on a suitable mill. Such powders can be used for dry seed dressing.

| Extruder granules | |
|---|---|
| active ingredient (I:II = 7:8) | 15% |
| sodium ligninsulfonate | 2% |
| carboxymethyl cellulose | 1% |
| kaolin | 82% |

The active ingredient is mixed with the additives and the mixture is ground and moistened with water. This mixture is extruded and subsequently dried in a stream of air.

| Coated granules | |
|---|---|
| active ingredient (I:II = 3:5) | 8% |
| polyethylene glykol (MG 200) | 3% |
| kaolin | 89% |

(MG = molecular weight)

In a mixer, the kaolin which has been moistened with polyethylene glycol is uniformly coated with the finely ground active ingredient to give non-dusty coated granules.

| Suspension concentrate | |
|---|---|
| active ingredient (I:II = 2:3) | 40% |
| propylene glycol | 10% |
| nonylphenol polyethylene glycol ether (15 mol of ethylene oxide) | 6% |
| sodium ligninsulfonate | 10% |
| carboxymethyl cellulose | 1% |
| silicone oil (in the form of a 75% aqueous emulsion) | 1% |
| water | 32% |

The finely ground active ingredient is homogeneously mixed with the adjuvants, giving a suspension concentrate from which suspensions of any desired dilution can be prepared by addition of water. Such dilute suspensions can be used for treating live plants and vegetable or animal products by spraying, watering or immersing and thus protecting them against attack by microorganisms.

BIOLOGICAL EXAMPLES

Fungicides always have a synergistic effect if the fungicidal activity of the combined formulation is greater than the sum of the activity of the individually applied fungicides.

The expected activity E for a given combined formulation, e.g. consisting of two fungicides, obeys the COLBY formula and can be calculated as follows (COLBY, L. R. "Calculating synergistic and antagonistic responses of a herbicide combination", Weeds 15, pp. 20–22), (LIMPEL et al., 1062 "Weeds control by ... certain combinations", Proc. NEWCL, Vol. 16, pp. 48–53): (g of a.i./ha = grams of active ingredient per hectoliter of spray mixture)

X = percentage activity of fungicide I at a rate of application of p g of a.i./ha
Y = percentage activity of fungicide II at a rate of application of q g of a.i./ha
E = expected activity of fungicides I+II at a rate of application of p+q g of a.i./ha then according to Colby:

$$E = X + Y - \frac{X \cdot Y}{100}$$

If the actually observed activity (O) is greater than that calculated, then the activity of the combined formulation is greater than additive, i.e. there is synergism.

EXAMPLE 1

Fungicidal Action Against *Helminthosporium gramineum* on Winter Barley Seed

Winter barley (cv. Hauter) which is infected with *Helminthosporium gramineum* is harvested from the field. The malt agar test reveals that 95% of the seeds are infected. These seeds are treated with mixtures of the active ingredients as shown in the following table. The ingredients are first dispersed in water and the dispersion is sprayed onto the seeds which are on a rotating disc. This procedure corresponds to methods which are customary in practice. Untreated seeds of the same origin are used as control.

Batches of 100 grains are sown, at a depth of 2 cm, in seed dishes (45×35×10 cm) which are filled with sterile field soil. Three replications of the test are run. The seed dishes are moistened and kept for 28 days at 2° C., with the exclusion of light. They are then transferred to a greenhouse 18° C./12° C. (day/night). Evaluation of infection is made (percentage of infected plants) 56 days after sowing. At this time, plants which are infected with *H. gramineum* show typical chlorotic stripes on the first leaf. The percentage of diseased plants in the treatments is established in relation to the percentage of infected, but untreated, plants and expressed as percentage of fungal attack.

TABLE 1

| Treat-ment | g of active ingredient/100 kg of seeds | | Fungal attack (%) | Effect E (calculated) (%) (COLBY) | Effect O (found) (%) |
|---|---|---|---|---|---|
| | Component I | Component II | | | |
| Comparison 1 | — | — | 100 | — | — |
| 2. | 0,43 | — | 68 | — | 32 |
| 3. | 1,7 | — | 43 | — | 57 |
| 4. | 3,4 | — | 38 | — | 62 |
| 5. | — | 0,5 | 85 | — | 15 |
| 6. | — | 1,0 | 79 | — | 21 |
| 7. | — | 2,0 | 58 | — | 42 |
| 8. | 0,43 | 0,5 | 55 | 42 | 45 |
| 9. | 0,43 | 1,0 | 49 | 46 | 51 |
| 10. | 1,7 | 2,0 | 22 | 75 | 78 |
| 11. | 3,4 | 0,5 | 26 | 68 | 74 |
| 12. | 3,4 | 1,0 | 25 | 70 | 75 |
| 13. | 3,4 | 2,0 | 12 | 78 | 88 |

As can be seen from Table 1, the treatments 8–13, in which components I and II had been varied over a wide range of the mixing ratios, exhibit a markedly enhanced, i.e. synergistic, effect.

Comparably enhanced effects, i.e. synergistic effects, are observed in the case of snow mould (*Gerlachia nivalis*) on wheat, barley and rye, against *Ustilago nuda* on barley, against *Tilletia caries* on wheat and against other seed- and soil-borne pathogens.

EXAMPLE 2

Fungicidal Action Against *Gerlachia nivalis*. Rye-Seed Treatment

For use as dry-dressing agents, the active ingredients are extended (=diluted) with powdered stone to give a finely particulate mixture which ensures uniform distribution on the surface of the seeds.

For carrying out the seed treatment, the infected seeds, together with the seed-dressing agent are put into a glass flask and the flask is sealed and shaken for 3 minutes.

Batches of 100 grains of rye are sown at a depth of 1 cm in 2 seed dishes, filled with standard soil, and the rye is grown in the greenhouse at a temperature of approx. 10° C. and a relative atmospheric humidity of approx. 95%. The daily illumination with artificial light (greenhouse lamp) is 15 hours.

Approx. 3 weeks after sowing, the plants are evaluated for disease symptoms. The application rates of the individual active ingredients and of the mixture as well as the test results can be seen from Table 1 below.

EXAMPLE 3

Fungicidal Action Against *Fusarium culmorum*. Wheat-Seed Treatment

The active ingredients are applied by wet or dry treatment.

For carrying out the seed treatment, the infected seeds and the seed-dressing agent are put into a glass flask, which is sealed and shaken for 3 minutes.

Batches of 100 grains of wheat are sown, at a depth of 1 cm, in 2 seed dishes filled with standard soil, and the wheat is grown in the greenhouse at a temperature of approx. 18° C. and 15 hours' daily exposure to artificial light.

Approx. 3 weeks after sowing, the plants are evaluated for disease symptoms.

The concentration of the individual active ingredients and of the mixture as well as the test results can be seen from Table 2.

TABLE 2

| Treatment No. | mg of active ingredient/kg of seeds | | Degree of effectiveness in the untreated control (%) |
|---|---|---|---|
| | Component I | Component II | |
| Example 2 (rye) | 1.5625 | — | 35% |
| | — | 1.5625 | 0% |
| | 0.78125 | 0.78125 | 59% |
| Example 3 (wheat) | 25 | — | 59% |
| | — | 25 | 64% |
| | 12.5 | 12.5 | 69% |
| Untreated control | — | — | 0% |

What is claimed is:

1. A composition for controlling or preventing infections by plant pathogenic fungi, containing a synergistic plant pathogenic fungicidally effective amount of a mixture of two active ingredient components I) and II), component I) being 4-(2,2-difluoro-1,3-benzodioxol-7-yl)-1H-pyrrole-3-carbonitrile of the formula (I)

[structural formula of component I]

component II) being α-[2-(4-chlorophenyl)ethyl]-α-(1,1-dimethylethyl-β-(1H-1,2,4-triazolyl)-1-ethanol of the formula (II)

[structural formula of component II]

or a salt thereof, the synergistic ratio by weight of I):II) being from 1:2.32 to 6.8:1, together with a suitable carrier.

2. A composition as claimed in claim 1, in which the ratio by weight of I):II) is from 4:1 to 1:2.

3. A method of controlling or preventing an infection of a plant or a part of a plant by plant pathogenic fungi, which comprises treating said plant, which is already infected or is liable to be infected, or said part of a plant, which is already infected or is liable to be infected, or the locus of said plant, with a synergistic fungicidally effective amount of a composition according to claim 1.

4. A method as claimed in claim 3, wherein said plant or said part of a plant is a plant propagation material.

5. A method as claimed in claim 4, wherein said plant propagation material is a seed.

6. A method according to claim 3, wherein the active ingredients are applied in direct succession.

7. A method of protecting materials of animal or vegetable origin against attack by plant pathogenic fungi, which comprises treating said materials with a synergistic fungicidally effective amount of a composition according to claim 1.

8. A method according to claim 7, wherein said materials of animal or vegetable origin is a storage good or timber.

9. A method according to claim 7, wherein said materials are storage goods of vegetable origin harvested from the natural life cycle.

10. A plant propagation material, the plants grown from which are protected against harmful plant fungi occurring in the soil, comprising a plant propagation material coated with a synergistic fungicidally effective amount of a composition according to claim 1.

11. The plant propagation material of claim 10, wherein the plant propagation material is a seed.

* * * * *